United States Patent [19]

Mora

[11] 3,950,519

[45] Apr. 13, 1976

[54] COMPOSITION AND METHOD OF TREATING ASTHMA

[76] Inventor: Rene M. Mora, 110 SW. 35th Ave., Miami, Fla. 33135

[22] Filed: Apr. 2, 1975

[21] Appl. No.: 564,322

Related U.S. Application Data

[63] Continuation-in-part of Ser. No. 442,855, Feb. 15, 1974, abandoned.

[52] U.S. Cl. .............................. 424/195; 424/196
[51] Int. Cl.² ................. A61K 35/78; A61K 35/04
[58] Field of Search ........................... 424/195, 196

[56] References Cited
OTHER PUBLICATIONS

Chemical Abstracts, Vol. 36:1662 [7], Vol. 56:10580i & 10581a, Vol. 57:10222g, Vol. 65:17010f, (1966).

Roig et al., "Plantas Medicinales de Cuba," pp. 222 and 223, (1945), Parte I, Published by Republica de Cuba Ministerio de Agricultura.

Primary Examiner—Donald B. Moyer
Attorney, Agent, or Firm—Clarence A. O'Brien; Harvey B. Jacobson

[57] ABSTRACT

An aqueous composition for the treatment of asthma contains from 35 to 50 grams cedar resin per liter of composition, and preferably includes coloring and flavoring additives. The composition is preferably administered in dosages up to 15 c.c. three times daily for periods up to about 20 days and can be repeated for further periods of up to 20 days, as necessary.

12 Claims, No Drawings

COMPOSITION AND METHOD OF TREATING ASTHMA

This is a continuation-in-part of application Ser. No. 442,855, filed February 15, 1974 now abandoned.

The present invention relates to a composition and method for the treatment of asthma and its symptoms, and, more particularly, to the treatment of extrinsic asthma caused by allergic hypersensitivity.

Asthma simply means attacks of shortness of breath. The term has been used for the clinical picture of shortness of breath due to any cause ranging from an enlarged thymus gland to heart failure, but excluding bronchitis with wheezing, tumors, foreign bodies in the air passages, and all other conditions imitating asthma. See, e.g., *Introduction to Lung Diseases*, American Lung Association (1973); *Introduction to Respiratory Diseases*, National Tuberculosis and Respiratory Disease Association (1969). Asthma is a condition of abnormal responsiveness of the air passages to certain substances and is manifested by a widespread narrowing of the smaller airways.

The form of asthma that is best understood is allergic or extrinsic asthma. Allergic asthma results from the sensitization of a hypersensitive or atopic individual to an allergen, usually a protein, in the form of an inhaled pollen, mold spore, animal dander, feather dust, lint, or insecticide, or, less commonly, to a food such as milk, seafood, nuts, or chocolate. Certain synthetic drugs such as aspirin, although not proteins, can also sensitize. Exposure to the specific allergen, even in minute quantities, produces an attack. Pathologically, in allergic asthma the lungs are distended and voluminous. The bronchi and bronchioles are full of tenacious mucus. Plugs of thick mucus block most of the terminal bronchioles. The goblet cells in the bronchial epithelium are increased in size and number. The muscle in the bronchial walls is hypertrophied and in the swollen tissues under the epithelium there is an infiltration of mononuclear cells and many eosinophils. The layer of tissue underlying the mucous membrane may become thickened.

Physically, after an exposure to the causative allergen, the chief symptom is shortness of breath, which may begin suddenly. The victim feels as if he is suffocating. He must sit up or stand and devote all his energy to breathing. As the attack approaches its end, a cough, at first slight and dry, becomes more marked and productive of considerable white sputum. Following an attack, the victim may experience considerable chest soreness. In very sensitive individuals, under certain circumstances an attack may persist into status asthmaticus, a condition of sustained shortness of breath which may last for days.

There are many drugs available for the symptomatic relief of asthma, e.g., bronchodilators, nebulized drugs and corticosteroids. However, although these drugs seem to relieve the immediate crises, they do little more than return the patient to his normal condition, which for asthmatic patients includes a continuing excess of mucus in the lungs. The patient therefore remains susceptible to similarly induced future crises if he again comes into contact with the allergenic agents. For long term relief, the only presently known technique is desensitization, which usually involves a course of injections of sequentially larger quantities of the sensitizing allergen over a period of eight weeks or more, with periodic reinforcement. However, there appears to be no known, effective method of treating allergic asthma which can result in a long-term remission, at least from 1 to 4 years and possibly longer, of the symptoms.

It is therefore an object of this invention to provide a composition and method of its administration for the treatment of extrinsic asthma which effects a long term remission of its symptoms.

It is another object of this invention to provide a composition and method of its administration which has the effect of cleaning the respiratory system of an asthmatic patient of excess mucus and thereby eliminating or greatly reducing the patient's susceptibility to future asthmatic attacks.

Other objects and advantages will become apparent from the following description and appended claims.

The objects of this invention are achieved by providing a composition for the treatment of extrinsic asthma which contains, as the active ingredient, cedar resin (as hereinafter described) in sufficient quantities that when the composition is administered over a sufficient period of time it functions as a potent antiasthmatic agent exhibiting expectorant action to aid in cleansing the lungs of excess mucus. Typically, the composition is administered in syrup form orally in dosages up to 15 cc three times a day for about 15 days in children under 18 years of age and for about 20 days in adults over 18 years of age. In adults, repetition of the treatment for another 20 days is sometimes indicated.

The cedar resin composition of the present invention is intended primarily for the treatment of extrinsic bronchial asthma induced generally by inhalation of external allergens. The composition has not demonstrated effectiveness in treating emotive asthma. Moreover, it should be noted that the composition is intended as a prophylactic treatment to bring about a long-term remission of the symptoms of extrinsic asthma and is not intended to instantaneously alleviate an asthma attack. Indeed, the cedar resin composition administration may be carried out concurrently with the administration of drugs intended to provide immediate relief for the symptoms of asthma, such as bronchodilators and corticosteroids, without contraindications. After about four years of experimental administration of the cedar resin composition to about 400 patients, no significant adverse side effects, such as hives, headaches, vomitus, abdominal pain or diarrhea, have been noted. In some cases, rhinitis may be present in some patients during the treatment, but it disappears rapidly. Mild itching in the eyes and tingling in the fingers are occasional, short-term side effects of the cedar resin composition.

The plant material useful in the present invention is a natural substance, characteristically sticky, and yellow or brown in color, which flows from the bark of the cedar tree. Specifically, the plant material referred to herein as cedar resin is obtained from *Cedrela Odorata* L (also known as Spanish Cedar), a member of the Meliaceous family, plants which are indigenous to South and Central America. The resin constitutes the gummy substance which escapes through cracks in the bark of the trunk when the tree is traumatized. It is obtained from the trunk in much the same manner as is the sap from maple trees or the rubber from rubber trees, i.e., it flows through the cracks in the bark and dries on the bark in a crystalloid formation (resembling rock candy) from which it may be gathered by hand or with tools. Once removed from the tree, the resin needs no special treatment for preservation (no refrigeration or special containers are needed) and will remain stable indefinitely. Chemically, cedar resin is a plant carbohydrate having a structure, as determined by infrared analysis, suggestive of polysaccharide with some carboxyl groups present. Quantitative elemental analysis indicates that the resin comprises, by weight, about 40% carbon, 50% oxygen, 6% hydrogen with the balance trace amounts of nitrogen, phosphorus, calcium, magnesium, sodium and potassium. Spectrographic analysis further indicates the presence of trace amounts of boron, copper, iron, strontium and silicon.

To prepare the preferred composition of the present invention, the cedar resin is combined with water and with a number of inactive ingredients in appropriate quantities which serve to improve the palatability and administrability of the cedar resin by improving its color, flavor, body, shelf life and the like. It will be appreciated that inasmuch as the ceder resin is the only active ingredient, it is likewise the only critical ingredient of the composition, preferably present in concentrations of 35 to 50 grams/liter. In one useful embodiment of the invention, the cedar resin is combined with the following ingredients in the appropriate proportions indicated:

Cedar Resin — 35–50 grams
Propylparaben (U.S.P.) — 0.25 gram
Methylparaben (U.S.P.) — 0.75 gram
Sucrose (cane sugar) — 80 grams
Red food color — 1 c.c.
Pure orange extract — 1½ c.c.
Water to make — 1,000 c.c.

The following example sets forth a typical method of preparing a suitable cedar resin containing antiasthmatic composition, and specifically the composition set forth above.

EXAMPLE I

Dissolve 0.25 gram propylparaben and 0.75 gram methylparaben in 1,000 c.c. of fresh water at 80°C with stirring as necessary. After the parabens have completely dissolved, permit the solution to return to room temperature. Add 35 grams of cedar resin and let stand for 4–5 days until the resin has substantially dissolved forming a water solution of the plant material. Filter the solution using a metal colander to remove any large undissolved particles and then filter again through a flannel cloth to remove undissolved fines. Check the specific gravity of the resulting solution at 30°C to confirm that it is 1010. Adjust the specific gravity, as necessary, by addition of more cedar resin to increase it or water to decrease it. To the adjusted solution add 80 grams of cane sugar (sucrose) and dissolve with stirring. Again, filter the solution through a flannel cloth. Transfer the solution to a glass or porcelain container and boil for about 5 minutes (foaming will occur). About ten minutes after boiling has stopped add 1 c.c. of red food color (e.g., Red Food Color commercially available from McCormick & Co., Inc. of Baltimore, Maryland, containing 2.5% U.S. Certified Food Color in water and propylene glycol) and 1½ c.c of pure orange extract (e.g., Pure Orange Extract commercially available from McCormick & Co., Inc. of Baltimore, Md., containing 80% alcohol, oil of orange and water). When the resulting composition has returned to room temperature it may be bottled for storage in conveniently sized, preferably amber colored, sterile containers.

Animal toxicity studies were conducted by injecting the cedar resin containing composition intraperitoneally into test mice, with other mice serving as controls. The behavior and appearance of both the test mice and control mice were normal. Selected test and control mice were sacrificed and their liver, lung, thymus, heart, spleen and kidneys removed for examination and pathological study. The gross appearance of all organs was normal and none showed evidence of toxicity or hypersensitivity.

The cedar resin composition specifically described herein, or other pharmaceutically satisfactory composition containing about 35–50 grams per liter cedar resin, may be conveniently administered to asthmatic patients. Specific dosages may vary with age of the patient and severity of the case. However, it is preferred to administer the composition orally three times daily, in dosages of 1 c.c. per year of age up to a maximum dosage of 15 c.c. three times daily. The minimum effective dose, irrespective of age except for infants whose cases must be considered individually, is about 5 c.c three times daily. For children under 18 years of age, treatment should extend for about 15 days. For adults over 18 years of age, treatment should continue for about 20 days, if the results are not totally satisfactory, after 15–60 days, preferably about 30 days, the treatment should be repeated for another period of about 20 days.

The cedar resin compositions of the present invention are primarily intended for the treatment of allergic bronchial asthma, i.e., asthma usually caused by allergic hypersensitivity of the person to foreign substances in the air—especially to plant pollens. The allergic reaction causes localized edema in the walls of the small bronchioles, secretion of thick mucus into their lumens, and spasm of their smooth muscle walls. These effects greatly increase the airway resistance to the alveoli. In addition, the bronchiolar diameter becomes even further reduced during expiration and then opens up to a certain extent during inspiration. Therefore, the asthmatic person usually can inspire quite adequately but has great difficulty expiring. This results in dyspnea, or "air hunger". The functional residual capacity and the residual volume of the lung become greatly increased during the asthmatic attack because of the difficulty in expiring air from the lungs. Over a long period of time the chest cage becomes permanently enlarged, causing a "barrel chest", and the functional residual capacity and residual volume also become permanently increased.

Without wishing to be bound to any particular theory, it is believed that the cedar resin composition is effective because it reduces and eliminates spasms of the alveolar sacs and respiratory bronchiole by reducing and eliminating mucus plugs which cause ciliary activity to stop and secretions to be retained. Specifically, it is believed that the cedar resin causes the mucus to fluidize and to become thinner, allowing ciliary activity to increase and secretions to be removed. This produces, at first, spasms of the alveolic sacs and the respiratory bronchile, similar to a mild asthma attack with coughing. The coughing results in high expectoration of mucus or spiral Curschmann until the mucus plugs are eliminated from the respiratory system. In children or adults only recently asthmatic, all excess mucus can be cleaned from the respiratory system by a single 15–20 day treatment. However, long term asthmatics require repeated treatments to completely clear their respiratory systems of excess mucus. Once cleared, however, even if the patients come in contact with the allergenic agents, since there is an absence of excess mucus, an asthmatic crisis does not develop. As previously indicated, the cedar resin composition and treatment of the present invention is intended to effect long-term remission of asthma symptoms, and is not a medicament for the temporary relief of asthmatic crises. Within the limits of 4 years of clinical testing, its long-term effectiveness has been confirmed.

The following examples set forth a few of the clinical experiences with the cedar resin composition of the present invention. In each case set forth the diagnosis was made over a clinical evaluation period of more than one year based on daily examinations. In each case the patients were followed carefully for about four years to observe the long term effects of the instant treatment. To each patient the following composition was administered orally in the dosages and with the frequency indicated:

Cedar Resin — 35 grams
Propylparaben (U.S.P.) — 0.25 gram
Methylparaben (U.S.P.) — 0.75 gram
Sucrose (cane sugar) — 80 grams
Red food color — 1 c.c.
Pure orange extract — 1½ c.c.
Water to make — 1,000 c.c.

EXAMPLE II

Female, 6 years old has been afflicted with allergic asthma induced by the shrubs and grass from the garden at her home since her second year of birth. This patient was administered 6 c.c. of the cedar composition three times a day, far from meals, for 16 days. During the fifth day of treatment she developed a mild asthma attack, and afterwards, up to the tenth day of treatment, she had great expectoration. For her last 4 days she did quite well. No recurrence of the asthma has been reported with this patient.

At the outset of treatment, the patient was given bronchodilator treatment which was slowly discontinued until no longer necessary. No adverse effects were observed as a result of the simultaneous treatment with bronchodilators and the cedar composition.

EXAMPLE III

Female, 46 years old, had a history of allergic asthma induced by climatic changes, particularly from dry to wet weather, since age 7 with intermittent intervals of months without asthma attacks. The patient began the treatment with the cedar composition taking 15 c.c. three times a day, far from meals, for 20 days. The patient had no expectoration during the first treatment. Thirty days after she finished the first treatment, she underwent a second treatment in the same manner with the same dosage and frequency and for the same 20 day period. The patient experienced some expectoration during the second treatment period. Following the second treatment, the patient has had no further bronchial asthma attacks for about 4 years.

At the beginning of both the first and second treatments, the patient was also administered bronchodilators and Cortisone. By the end of the treatments, these medications had become unnecessary. No adverse effects were noted during or after the cedar composition treatments as a result of concurrent administration of the bronchodilators and the Cortisone.

EXAMPLE IV

Patient was a 4 year old with severe allergic asthma induced by inhalation of limestone dust since 1 year of age. Bronchodilators P. O. were oftentimes not enough to relieve the patient's frequent attacks to the extent that Cortisone I.M. and Adrenaline I.M. were needed. Patient was administered five c.c. of the cedar composition three times daily for 15 days. During his treatment with the cedar composition the patient developed unexplained high temperature for 2 days. Following the period of high temperature the patient had considerable expectoration. After the treatment was concluded, the patient was free of asthma except for one mild attack he suffered during the course of a cold about 2 months following treatment. Generally, the patient increased in weight and did quite well after the cedar composition treatment was concluded.

EXAMPLE V

Patient was a 4 year old female with allergic asthma since birth. Patient experienced very frequent asthma attacks induced by limestone dust and pet hairs (especially dogs) and had previously undergone several and frequent treatments with auto-vaccine and stock-vaccine with only mild and temporal relief of her symptoms. This girl was administered the cedar composition for 16 days, taking 5 c.c. three times a day. The patient experienced only mild expectoration and complained of some itching around both eyes. Following treatment, the patient's appetite increased and both her height and weight increased. No further asthma attacks were experienced.

EXAMPLE VI

Patient was a 48 year old male with a history of bronchial asthma since age 23. This patient experienced only mild asthma attacks during the summer. However, at the beginning of the winter, during each change in weather, he had very severe asthma attacks brought on by exposure to the cold weather. His records indicated that he had been treated on at least 12 separate occasions in the Emergency Room and had been admitted to the hospital three times with very severe asthma attacks. The last time, he was admitted for 18 days.

The patient's initial treatment with the cedar composition employed a dosage of 15 c.c. three times daily, far from meals, for 22 days. At the beginning of treatment the patient used bronchodilators and Cortisone. By the end of the first treatment, he needed only some bronchodilators. His condition following the first treatment had improved approximately 40%. Thirty days after the first treatment he was again treated using 15 c.c. three times daily for 15 days. This time the patient had considerable expectoration, but no adverse effects were observed. Six weeks after completing the second treatment the patient had a cold accompanied by very severe expectoration. Since that time the patient has had no attacks of bronchial asthma.

EXAMPLE VII

Patient was a 57 year old male with allergic asthma induced by household insecticides and pesticides since he was 2 years old. This patient was given 15 c.c. of the cedar composition three times daily, far from meals, for 20 days. During his fifth day of treatment, the patient developed a moderate asthma attack with yellow and grayish expectoration in very great amounts. An Eosinophil count in his sputum and in his blood revealed 73% Eosinophil in the sputum and 13% Eosinophil in the blood. At the end of the first treatment, the patient appeared to be quite well. However, about 15 days later he developed a crisis and had to receive treatment in the Emergency Room. About 7 days after the crisis, the patient resumed treatment with the cedar composition, taking 15 c.c. three times daily for 20 days. He experienced considerable expectoration during this period. Following the second treatment the patient did quite well with the single exception that insecticides caused a tightening in his airway, but no asthma attack. Patient's Eosinophil count in sputum remains about 5% and in blood 4%.

EXAMPLE VIII

Patient was a 23 year old female asthmatic since 20 years of age. The patient was allergic to many things, particularly rice and milk, and, during her last 3 years, has had rhinorrhea almost daily. She was administered 15 c.c. three times daily of the cedar composition, far from meals, for 15 days. At about the fifth day, she began to have expectoration and a mild asthma attack, needing bronchodilators by aspiration and by mouth for relief. After that, she had mild expectoration for about 8 more days. Ten days after starting with the cedar composition, the rhinorrhea disappeared completely.

Patient was doing quite well until about 2 months after completing treatment she had an I.V.P. during which she developed a severe asthma attack which required I.V. bronchodilators. The rhinorrhea began again and the cedar composition treatment was repeated in the same manner as before. This second time, the patient had more expectoration than before. The asthma disappeared completely but the rhinorrhea continued as before. Patient's appetite and weight increased. During both treatments, the patient complained of mild itching around the eyes, the mouth and in both hands. However, the itching disappeared both times by the end of the respective treatments.

EXAMPLE IX

Patient was a 14 month old male severe asthmatic since 6 months of age with known allergies to dust and pet hairs. Four months before starting the cedar composition treatment, the patient required I.M. Cortisone almost daily and I.M. Adrenaline almost twice a week. Due to the age of the patient, treatment started with only 3 c.c. of the cedar composition three times daily, but was continued for 20 days. Throughout treatment, the patient received bronchodilator P.O., Cortisone I.M. and Adrenaline I.M. as necessary. The patient vomited regularly. However, it is very frequent in such young patients, who do not know how to expectorate large amounts of mucus, to vomit one or two times daily during cedar composition treatment. Aside from the vomitings, no other adverse effects were noted. Following treatment, there was no recurrence of the patient's asthma condition.

While the present invention has been described with reference to particular embodiments thereof, it will be understood that numerous modifications can be made by those skilled in the art without departing from the scope of the invention. Accordingly, all modifications and equivalents may be resorted to which fall within the scope of the invention as claimed.

What is claimed as new is as follows:

1. An aqueous composition for treating allergenically induced asthma in human patients containing, as the only active ingredient, 35 to 50 grams of cedar resin obtained from *Cedrela Odorata* per liter of composition, said composition also including coloring and flavoring additives.

2. A composition, as claimed in claim 1, consisting essentially of the following ingredients in the proportion range indicated:
   Cedar Resin — 35–50 grams
   Propylparaben (U.S.P.) — 0.25 gram
   Methylparaben (U.S.P.) — 0.75 gram
   Sucrose (cane sugar) — 80 grams
   Red food color — 1 c.c.
   Pure orange extract — 1½ c.c.
   Water to make — 1,000 c.c.

3. A method of treating allergenically induced asthma in human patients afflicted therewith comprising orally administering to said patients an aqueous composition containing, as the only active ingredient, 35 to 50 grams of cedar resin obtained from *Cedrela Odorata* per liter of composition in dosages of from 3 to 15 c.c. of said composition three times daily for at least 15 days.

4. A method, as claimed in claim 3, wherein said composition further includes coloring and flavoring additives.

5. A method, as claimed in claim 3, wherein each said dosage is 1 c.c. per year of age of the patient from a minimum of 5 c.c. up to a maximum of 15 c.c.

6. A method, as claimed in claim 4, wherein said composition consists essentially of the following ingredients in the proportion range indicated:
   Cedar Resin — 35–50 grams
   Propylparaben (U.S.P.) — 0.25 gram
   Methylparaben (U.S.P.) — 0.75 gram
   Sucrose (cane sugar) — 80 grams
   Red food color — 1 c.c.
   Pure orange extract — 1½ c.c.
   Water to make — 1,000 c.c.

7. A method, as claimed in claim 5, comprising administering said composition for periods of up to about 20 days.

8. A method, as claimed in claim 5, comprising administering said composition for a first period of from 15 to 20 days followed by administering said composition in dosages of from 5 to 15 c.c. three times daily for a second period of from 15 to 20 days.

9. A method, as claimed in claim 8, wherein the beginning of said second period follows by about 15 to 60 days, the end of said first period.

10. A method, as claimed in claim 9, wherein the beginning of said second period follows by about 30 days, the end of said first period.

11. A method, as claimed in claim 8, wherein said composition consists essentially of the following ingredients in the proportion range indicated:
   Cedar Resin — 35–50 grams
   Propylparaben (U.S.P.) — 0.25 gram
   Methylparaben (U.S.P.) — 0.75 gram
   Sucrose (cane sugar) — 80 grams
   Red food color — 1 c.c.
   Pure orange extract — 1½ c.c.
   Water to make — 1,000 c.c.

12. A method, as claimed in claim 9, wherein said composition consists essentially of the following ingredients in the proportion range indicated:
   Cedar Resin — 35–50 grams Propylparaben (U.S.P.) — 0.25 gram
Methylparaben (U.S.P.) — 0.75 gram
Sucrose (cane sugar) — 80 grams
Red food color — 1 c.c.

Pure orange extract — 1½ c.c.
Water to make — 1,000 c.c.

\* \* \* \* \*